United States Patent [19]

Pomot et al.

[11] 4,078,051
[45] Mar. 7, 1978

[54] CROSS-LINKED STARCH COATED ANTIPERSPIRANT DERIVATIVE OF ALUMINUM, PROCESS FOR ITS PREPARATION AND ANTIPERSPIRANT COMPOSITION CONTAINING SAME

[75] Inventors: Jean Pomot, Mouans Sartoux; Jean-Philippe Chalaye, Maisons-Alfort, both of France

[73] Assignee: L'Oreal, Paris, France

[21] Appl. No.: 619,475

[22] Filed: Oct. 3, 1975

Related U.S. Application Data

[63] Continuation-in-part of Ser. No. 438,946, Feb. 1, 1974, abandoned.

[30] Foreign Application Priority Data

Feb. 5, 1973 Luxembourg ............................ 66959

[51] Int. Cl.$^2$ ........................ A61K 9/62; A61K 7/38

[52] U.S. Cl. ........................................ 424/35; 424/46; 424/47; 424/68

[58] Field of Search ................... 424/68, 47, 35, 46

[56] References Cited

U.S. PATENT DOCUMENTS

| 3,664,963 | 5/1972 | Pasin | 424/34 |
| 3,691,271 | 9/1972 | Charle | 252/522 X |

Primary Examiner—Dale W. Ore
Attorney, Agent, or Firm—Cushman, Darby & Cushman

[57] ABSTRACT

An antiperspirant agent having a delayed antiperspirant activity comprises micro-crystals of an antiperspirant derivative of aluminum coated with starch partially crosslinked by etherification. The antiperspirant agent is present in the composition in amounts of about 2-8 weight percent thereof. The composition can be packaged as an aerosol.

17 Claims, No Drawings

CROSS-LINKED STARCH COATED ANTIPERSPIRANT DERIVATIVE OF ALUMINUM, PROCESS FOR ITS PREPARATION AND ANTIPERSPIRANT COMPOSITION CONTAINING SAME

This application is a continuation-in-part of our application Ser. No. 438,946, filed Feb. 1, 1974 now abandoned.

The present invention relates to a new product usefully employed, principally, as a delay-action antiperspirant agent, to a process of producing this product, and to an antiperspirant composition, packaged in the form of an aerosol, which contains this product.

For many years, the use of antiperspirant compositions packaged in the form of an aerosol, has gained wide acceptance. Such antiperspirant compositions are generally composed of an antiperspirant derivative of aluminum such as, for example, micronized basic aluminum hydrochloride suspended in the aerosol propellant, and a perfume dissolved in the propellant, i.e., the continuous phase of the aerosol composition. Further it has been known to include in these compositions such adjuvants as bactericides which function as deodorants, emollients and suspension agents to promote or enhance homogeneity of the composition and thereby facilitate its passage through the distribution valve of the aerosol container.

However, conventional type antiperspirant compositions packaged in the form of an aerosol, exhibit a certain number of significant disadvantages. For instance, because of its great solubility in water, conventional micronized antiperspirant derivatives of aluminum, when applied to the skin, dissolve essentially instantly and completely on contact with perspiration. Consequently their antiperspirant activity is essentially immediate, but disadvantageously of only short duration.

Thus the antiperspirant effect is dissipated rapidly which often requires the user to make several repeated applications of the antiperspirant composition throughout the day.

In an effort to overcome this drawback, manufacturers have at times resorted to including in such compositions antiperspirant derivatives of aluminum in quantities greater than is in fact necessary to control perspiration.

However, after application to the skin, the microcrystals of the aluminum derivative when in direct contact with the perspiration, produce, locally, very concentrated solutions which often cause irritations to users having sensitive skin.

Another disadvantage of conventional aerosol type antiperspirants, which contain both micro-crystals of antiperspirant derivatives of aluminum, in suspension in the propellant, and a perfume in solution in the latter, is that frequently a chemical reaction takes place between these two components, with the result that the perfume is often destroyed or changed, especially during storage of the packaged aerosol composition. Consequently, certain perfumes which are particularly sensitive to this type of destructive action cannot be used even though their use is particularly desirable.

Further, because of the irritant effect of antiperspirant derivatives of aluminum, certain disadvantages have been noted among those required to handle significant quantities of these materials, particularly during the production and packaging of antiperspirant compositions in the form of conventional aerosols.

It has now been discovered that the above disadvantages can be avoided by using as the antiperspirant agent in aerosol composition, not a micronized antiperspirant derivative of aluminum in the free state, but rather particles of a hygroscopic antiperspirant derivative of aluminum having a coating of a polymer whose rate of solubilization in water at human body temperature is such that the liberation of the antiperspirant derivative of aluminum is controllably delayed, i.e., it provides a progressive liberation of the antiperspirant derivative during contact with perspiration. Moreover, when the product according to the present invention is employed in aerosol compositions, the antiperspirant derivative of aluminum is isolated from the other components of the aerosol which are in solution or in suspension in the propellant.

To obtain the desired effects, the particles of the coated micro-crystals of the antiperspirant derivative of aluminum must possess certain chemical and physical properties. First, it is necessary that the coating material exhibit essentially no reactivity with the antiperspirant derivative of aluminum, which is generally not the case for a majority of polymers and especially for certain natural polymers, such as polypeptides or gums such as gum arabic. It is also necessary that polymer coating exhibit sufficiently slow swelling and dissolution characteristics in water or in perspiration at human body temperature so as to liberate only progressively the antiperspirant derivative of aluminum coated therewith. Moreover, when the coated antiperspirant derivative of aluminum is employed in an aerosol, it is necessary that the polymer coating material be completely insoluble and not swell up in the propellant, the latter generally comprising a mixture of fluoronated hydrocarbons such as those known under the trademark "FREON", and that it be impermeable to the propellant so that no other component in solution in the propellant, and notably the perfume, can come into contact with the antiperspirant derivative of aluminum, during storage in the aerosol container.

In addition to these requirements, it is preferable that the polymer coating material exhibit some cosmetic properties itself, and especially be a softener for the skin. Materials capable of satisfying these requirements are certain types of starch partially crosslinked by etherification.

Thus, the present invention relates principally to a delay-action antiperspirant agent comprising microcrystals of a basic aluminum halide coated with a starch partially crosslinked by etherification. The basic aluminum halide is basic aluminum hydrochloride or basic aluminum hydrobromide.

The partially crosslinked starch used in the present invention can be prepared according to a well known process described in the literature, particularly by the action on starch, in a basic aqueous medium, of a bifunctional reagent such as an epihalohydrin, a di-halohydrin, a dihalogenated ether or a dihalogenated lower alkane, for example epichlorohydrin, propylene dichloride, ethylene dibromide, dichloropentane, dichlorobutane, dichloro diethyl ether, and similar bifunctional reagents.

The partially crosslinked starches employed in the present invention are particularly those containing about one crosslink per 100 to 2000 glucose units present in the starch, and more particularly those containing one crosslink per about 150–200 to about 1000–2000 glucose units. For example, the starches partially crosslinked with epichlorohydrin are particularly those which are prepared from one part by weight of epichlorohydrin for about 200–3500 parts by weight of starch, and more particularly prepared from one part by weight of epichlorohydrin for about 250–350 to about 1500–3500 parts by weight of starch.

The starches which are used to prepare the crosslinked starches employed in the present invention may be of various origins, for example, cornstarch or starches of rice, manioc, sorghum or potato. In particular, ordinary native cornstarch partially crosslinked by etherification with epichlorohydrin can be used.

A starch crosslinked with epichlorohydrin in the present invention can typically be prepared as follows: The starch can be suspended in water at 34–44% solids and the alkalinity adjusted to a pH of about 11 with alkali, for example sodium hydroxide. Epichlorohydrin in predetermined amounts can then be added and the resulting reaction mixture is agitated until the required inhibition is obtained. Then the starch slurry is acidified to stop the reaction, filtered, washed to remove reaction by-products and dried.

The product of the present invention has the property of exhibiting a considerable delay to hydration when it is placed in the presence of water at a temperature lower than 50° C.

In order to facilitate its use in aerosols, the product of the present invention can advantageously be produced in the form of a powder, consisting of finely divided particles having a diameter between 10–50 microns, and preferably between 20–30 microns. This dimension is particularly favorable to the passage through the distribution valve of the aerosol container and lends itself advantageously to good adherence of the particles to the skin.

The present invention also relates to a process for obtaining the product defined above, the said process comprising introducing into a current of air at an elevated temperature, generated for example in an atomizer drier, an aqueous gel of the partially crosslinked starch defined above containing an antiperspirant derivative of aluminum. The aqueous gel of crosslinked starch can be obtained by producing a suspension of said starch in cold water; heating this suspension, with agitation, to a temperature between 80°–90° C and preferably to about 85° C so as to impart fluidity to the gel; and then adding thereto the antiperspirant derivative of aluminum, either in the form of crystals, or in the form of an aqueous solution of conventional concentration, for example a 30 to 55% (by weight) solution of basic aluminum hydrochloride. The gel thus obtained is maintained at a temperature between 80°–90° C during its introduction into the atomizer drier. The temperature of the air at the inlet to the atomizer drier, which can be of conventional design, can be maintained between 200°–230° C, and the exit temperature can be maintained, for example, at 110°–120° C.

The concentration of the antiperspirant derivative of aluminum employed in the starch gel can be determined by the weight ratio of the antiperspirant derivative of aluminum to starch (dry basis) that is desired in the final product. Conveniently, this weight ratio is advantageously between 1:10 and 1:1.

The concentration of crosslinked starch in the aqueous gel ranges between about 5–30 and, preferably between 10–15, weight percent thereof.

Further, the weight ratio of the antiperspirant derivative of aluminum to crosslinked starch influences the rate of liberation of the antiperspirant derivative of aluminum in perspiration, this being all the more slow as this ratio is low. Moreover, this rate of liberation of the antiperspirant derivative of aluminum is also influenced by the degree of crosslinking of the starch employed.

One of the important characteristics of the present invention is to provide a control of the rate of solubilization of the antiperspirant product in contact with perspiration by varying the ratio between the respective weights of the antiperspirant derivative of aluminum and the crosslinked starch coating therefor, and to vary the degree of crosslinking of the starch employed and by producing thus on the skin, so as to protect against perspiration, a potential reserve of antiperspirant agent capable of exercising its activity over a prolonged period.

The present invention also relates to an antiperspirant composition comprising in an appropriate cosmetic vehicle or carrier, the product defined above.

The expression "cosmetic vehicle" as employed in the present invention includes all the components of the composition other than the active component, which components thus serve as the vehicle for this active product. The term "cosmetic" as employed in the present invention indicates simply that this vehicle must be able to be applied without any deleterious effect on the skin of the user. The components constituting the vehicle of the deodorant or antiperspirant compositions of the present invention are described in well known works on cosmetology and are designated generally by the expression "cosmetic vehicle". See for example Handbook of Cosmetic Science, cited above, page 332, 9th line from the bottom.

The antiperspirant compositions according to the present invention are principally compositions packaged in the form of aerosols which include, in addition to the product coated in accordance with the invention, an aerosol propellant agent. This propellant agent functions to provide within the aerosol container a pressure sufficient to permit progressive release of the contents of the container through the distribution valve of said container.

It is known that propellant agents generally comprise a liquid or liquified fluorinated hydrocarbon or a mixture thereof such as those sold under the name "FREON". These aerosol propellant agents are well known and are referred to in the present invention as a fluorohydrocarbon aerosol propellant agent. These propellant agents are principally fluoronated derivatives of methane or ethane and the propellants most often utilized are dichlorodifluoromethane (Freon 12), trichlorofluoromethane (Freon 11), and dichlorotetrafluoroethane (Freon 114). In practice, there is generally used either a mixture of Freon 11 and 12 or a mixture of Freon 12 and 114.

It is also well known that there can also be used as a propellant agent, $CO_2$ or nitrous oxide under pressure, in combination with a fluorohydrocarbon propellant agent in which the $CO_2$ or nitrous oxide is partially dissolved. Thus there can be employed, for example, as the aerosol propellant agent, Freon 11 and $CO_2$, or Freon 11 and nitrous oxide; see, for instance, Belgium Pat. No. 763,982.

Publications relating to the production of cosmetic compositions, packaged in the form of aerosols, and in particular those employing fluorohydrocarbon propellant agents, include the work of Hibbot, Handbook of Cosmetic Science, Pergamon Press (1963), Chapter XXIV, as well as the references mentioned in this chapter.

The cosmetic compositions in the form of aerosols according to the present invention can contain, for example, other active components and propellant agents, a perfume, a suspension agent to assist the homogeneity of the mixture such as colloidal silica, and an emollient such as isopropyl palmitate or myristate, or a mixture of these various cosmetic adjuvants for aerosols.

The cosmetic vehicle, when the composition is in the form of an aerosol, is then principally constituted by the aerosol propellant agent, and optionally the perfume, emollient and/or suspension agent.

Additionally, the antiperspirant composition in the form of an aerosol according to the present invention can contain a conventional bactericidal deodorant agent such as, for example, Irgason D.P. 300 (2,4,4'-trichloro-2'-hydroxy diphenyl ether).

Bactericidal deodorant agents used in the deodorant compositions are described in the literature such as the Handbook of Cosmetic Science, pages 332-334. One of the most well known deodorant agents is hexachlorophene.

The perfumes useful in the antiperspirant compositions of the present invention are well known and are disclosed, for instance, in the work of Heizka, International Encyclopedia of Aerosol Packaging, Pergamon, Oxford (1965).

Thus, in the antiperspirant compositions of the present invention, there can be employed, for example, perfumes sold under the following names: Colmen 13182 g and Leralia 18770 (Firmenich), Vervia C7 and 20247 (Creat Aromatiques), VIC 8 and F.N. 3083 (IFF) and E1048 (Aromescence).

The compositions of the invention can also be presented in the form of powders called "talcs".

The preparation of these "talcs", and the nature of cosmetic vehicles used in such compositions are described, for example, in the Handbook of Cosmetic Science, cited above, particularly at pages 339-344.

In addition to the active component, these powders can contain a cosmetic vehicle constituted by talc, which is the most abundant component (60-90 weight percent, generally), perfumes and generally at least one of the following components in the form of a suitably ground powder: titanium oxide, zinc oxide, kaolin, collidal silica, chalk, calcium phosphate, magnesium carbonate, zinc stearate and magnesium stearate.

The coated antiperspirant derivative of this invention can be present in the antiperspirant composition in amounts ranging between 2-8, preferably between 3-5, weight percent thereof.

In another embodiment of the present invention, the antiperspirant composition comprises, in addition to the product of the invention, a perfume stable in the presence of antiperspirant derivatives of aluminum and an antiperspirant agent other than the product of the present invention so as to provide a composition exhibiting both immediate action and delayed action against perspiration.

In this embodiment a predetermined quantity of micronized antiperspirant derivative of aluminum in the form of crystals, either not coated or coated with degraded starch, which is immediately soluble in perspiration, such as a starch of waxy maize hydrolyzed to a Stormer viscosity of 85, such as that commercially available under the name "AMIOCA" by National Starch Company, or ordinary cornstarch hydrolyzed to a Stormer viscosity of 65, such as that commercially available under the mark "FLUITEX" by National Starch Company or dextrin, can be added to predetermined quantities of the product of the present invention.

The compositions using in combination the antiperspirant product of the present invention exhibiting a delayed action with another antiperspirant agent without a delayed effect provides an effective action against perspiration for a time determined as a function of the relative amount of antiperspirant agents with and without the delay effect. While a wide range of relative amounts of these agents can be employed, it has been found advantageous to employ them in a ratio of between about 10:1 and 1:1, preferably between 2:1 and 1:1 parts by weight of the product of this invention per part by weight of said another antiperspirant agent exhibiting essentially no or little delayed action.

The following examples illustrate the preparation of products according to the invention as well as their use in antiperspirant aerosol formulations.

EXAMPLE A 100 g of ordinary cornstarch crosslinked with about 0.15 weight percent epichlorohydrin are suspended in 900 centiliters of distilled water. The suspension is heated with vigorous agitation up to a temperature of 85° C, at which temperature there is observed partial gelling of the starch and an increase in the viscosity of the mixture. 25 g of crystallized basic aluminum hydrochloride are then added, which dissolve instantly.

The resulting solution is maintained at 85° C and is then charged into the feed end of an atomizer drier by means of an intermediate peristaltic pump. The temperature of the air at the inlet of the atomizer drier is maintained at 215° C during the time of atomization, the exit temperature being between 110°-115° C.

At the end of the operation, there are removed from the cyclone of the atomizer drier, 120 g of a fine powder comprising particles having a diameter between 15-40 microns and having the following composition:

| Basic aluminum hydrochloride: | 1 pbw |
|---|---|
| Starch: | 4 pbw |

This powder is tested to measure by a conductivity meter its rate of dissolution in water at 37° C and at a pH of 6. The test shows that 50% of the product is solubilized after 2 hours of contact, 75% after 10 hours, and that 25 hours are required for total dissolution.

EXAMPLE B 100 g of cornstarch crosslinked with about 0.25 weight percent epichlorohydrin having a degree of crosslinking greater than that of the starch of Example A, are suspended in 900 centiliters of distilled water. The suspension is vigorously agitated and progressively brought to a temperature of 85° C. At this stage, a partial dissolution of the starch and an increase in viscosity of the mixture occurs.

With continued agitation, 50 g of crystallized basic aluminum hydrochloride are added thereto.

The resulting solution, maintained with agitation at a temperature of 85° C is then dried with atomization under the same conditions as those described in Example A. From the cyclone of the atomizer drier 142 g of fine powder are recovered. The individual particles of the powder have a diameter between 10–40 microns and have the following composition:

| | |
|---|---|
| Basic aluminum hydrochloride: | 1 pbw |
| Starch: | 2 pbw |

This powder when tested to measure its rate of dissolution in 37° C water at a pH of 6 reveals that 75% of the basic aluminum hydrochloride is solubilized after 3.5 hours of contact, with essentially total dissolution occurring in 15 hours.

EXAMPLE C

In accordance with procedures similar to those described in Example A, 100 g of basic aluminum hydrochloride are coated with 100 g of starch crosslinked with 0.5 weight percent epichlorohydrin.

EXAMPLE D

In accordance with procedures similar to those described in Example A, 100 g of basic aluminum hydrobromide are coated with 150 g of starch crosslinked with 0.4 weight percent epichlorohydrin.

EXAMPLE E

In accordance with procedures similar to those described in Example A, 50 g of basic aluminum hydrobromide are coated with 200 g of starch crosslinked with 0.12 weight percent epichlorohydrin.

EXAMPLE F

In accordance with procedures similar to those described in Example A, 100 g of basic aluminum hydrochloride are coated with 500 g of starch crosslinked with 0.1 weight percent epichlorohydrin.

EXAMPLE G

In accordance with procedures similar to those described in Example A, 100 g of basic aluminum hydrochloride are coated with 600 g of starch crosslinked with 0.07 weight percent epichlorohydrin.

EXAMPLE H

In accordance with procedures similar to those disclosed in Example A, 100 g of basic aluminum hydrobromide are coated with 800 g of starch crosslinked with 0.06 weight percent epichlorohydrin.

EXAMPLE I

In accordance with procedures similar to those disclosed in Example A, 50 g of basic aluminum hydrochloride are coated with 500 g of starch crosslinked with 0.04 weight percent epichlorohydrin.

EXAMPLE J

In accordance with procedures similar to those described in Example A, 100 g of basic aluminum hydrochloride are coated with 1000 g of starch crosslinked with 0.03 weight percent epichlorohydrin.

EXAMPLE K

In accordance with procedures similar to those disclosed in Example A, 50 g of basic aluminum hydrochloride are coated with 100 g of starch crosslinked with 0.4 weight percent propylene dichloride.

EXAMPLE L

In accordance with procedures similar to those disclosed in Example A, 25 g of basic aluminum hydrochloride are coated with 75 g of starch crosslinked with 0.25 weight percent propylene dichloride.

EXAMPLE M

In accordance with procedures similar to those disclosed in Example A, 100 g of basic aluminum hydrochloride are coated with 200 g of starch crosslinked with 0.4 weight percent ethylene dibromide.

EXAMPLE N

In accordance with procedures similar to those disclosed in Example A, 50 g of basic aluminum hydrochloride are coated with 300 g of starch crosslinked with 0.3 weight percent ethylene dibromide.

EXAMPLE O

In accordance with procedures similar to those disclosed in Example A, 25 g of basic aluminum hydrobromide are coated with 150 g of starch crosslinked with 0.25 weight percent ethylene dibromide.

EXAMPLE P

In accordance with procedures similar to those disclosed in Example A, 100 g of basic aluminum hydrochloride are coated with 200 g of starch crosslinked with 0.35 weight percent dichlorobutane.

EXAMPLE Q

In accordance with procedures similar to those described in Example A, 100 g of basic aluminum hydrochloride are coated with 300 g of starch crosslinked with 0.25 weight percent dichlorobutane.

EXAMPLE R

In accordance with procedures similar to those disclosed in Example A, 25 g of basic aluminum hydrobromide are coated with 100 g of starch crosslinked with 0.15 weight percent dichlorobutane.

EXAMPLE S

In accordance with procedures similar to those disclosed in Example A, 50 g of basic aluminum hydrochloride are coated with 100 g of starch crosslinked with 0.3 weight percent dichlorodiethylether.

EXAMPLE T

In accordance with procedures similar to those disclosed in Example A, 25 g of basic aluminum hydrobromide are coated with 100 g of starch crosslinked with 0.2 weight percent dichlorodiethylether.

EXAMPLE U

In accordance with procedures similar to those disclosed in Example A, 100 g of basic aluminum hydrochloride are coated with 1000 g of starch crosslinked with 0.1 weight percent dichlorodiethylether.

EXAMPLE V

In accordance with procedures similar to those disclosed in Example A, 30 g of basic aluminum hydrochloride are coated with 120 g of starch crosslinked with 0.2 weight percent dichloropentane.

EXAMPLE W

In accordance with procedures similar to those disclosed in Example A, 25 g of basic aluminum hydrochloride are coated with 125 g of starch crosslinked with 0.15 weight percent dichloropentane.

All the coated basic aluminum halide antiperspirant agents obtained in accordance with the preceding examples have a sufficiently slow solubility, at a temperature of 37° C, to permit progressive release of the active component for a period up to several hours.

EXAMPLE 1

An antiperspirant composition packaged under pressure as an aerosol is prepared by admixing the following components:

| | |
|---|---|
| Basic aluminum hydrochloride coated as in Example A, powder | 4.00 g |
| Colloidal silica (Aerosil 300-Degussa) | 0.30 g |
| Perfume | 0.50 g |
| Isopropyl myristate | 5.20 g |
| Trichlorofluoromethane | 45.00 g |
| Dichlorodifluoromethane | 45.00 g |
| | 100.00 g |

EXAMPLE 2

An antiperspirant composition packaged under pressure as an aerosol is prepared by admixing the following components:

| | |
|---|---|
| Basic aluminum hydrochloride coated as in Example A, powder | 4.00 g |
| Colloidal silica (Aerosil R972-Degussa) | 0.30 g |
| Irgosan DP 300 | 0.10 g |
| Perfume | 0.60 g |
| Isopropyl palmitate | 5.00 g |
| Trichlorofluoromethane | 45.00 g |
| Dichlorodifluoromethane | 45.00 g |
| | 100.00 g |

EXAMPLE 3

An antiperspirant composition packaged under pressure as an aerosol is prepared by admixing the following components:

| | |
|---|---|
| Basic aluminum hydrochloride coated as in Example A, powder | 4.00 g |
| Basic aluminum hydrochloride (not coated) | 2.00 g |
| Colloidal silica (Aerosil 300-Degussa) | 0.30 g |
| Perfume | 0.70 g |
| Isopropyl myristate | 3.00 g |
| Trichlorofluoromethane | 54.00 g |
| Dichlorodifluoromethane | 36.00 g |
| | 100.00 g |

EXAMPLE 4

An antiperspirant composition packaged under pressure as an aerosol is prepared by admixing the following components:

| | |
|---|---|
| Basic aluminum hydrochloride coated as in Example B, powder | 4.00 g |
| Basic aluminum hydrochloride (not coated) | 2.00 g |
| Colloidal silica (Aerosil R972-Degussa) | 0.30 g |
| Absolute ethyl alcohol | 20.00 g |
| Perfume | 0.70 g |
| Isopropyl palmitate | 3.00 g |
| Trichlorofluoromethane | 42.00 g |
| Dichlorodifluoromethane | 28.00 g |
| | 100.00 g |

EXAMPLE 5

An antiperspirant composition packaged under pressure as an aerosol is prepared by admixing the following components:

| | |
|---|---|
| Basic aluminum hydrochloride coated as in Example A, powder | 2.00 g |
| Basic aluminum hydrochloride coated with starch hydrolyzed to a Stormer viscosity of 85 (no delay effect) of waxy maize | 2.00 g |
| Colloidal silica (Aerosil 300-Degussa) | 0.20 g |
| Perfume | 0.60 g |
| Isopropyl myristate | 5.20 g |
| Trichlorofluoromethane | 45.00 g |
| Dichlorodifluoromethane | 45.00 g |
| | 100.00 g |

EXAMPLE 6

An antiperspirant composition packaged under pressure as an aerosol is prepared by admixing the following components:

| | |
|---|---|
| Basic aluminum hydrochloride coated as in Example B, powder | 2.00 g |
| Basic aluminum hydrochloride coated with ordinary cornstarch hydrolyzed to a Stormer viscosity of 65 (no delay effect) | 2.00 g |
| Colloidal silica (Aerosil R972-Degussa) | 0.30 g |
| Irgosan DP 300 | 0.10 g |
| Perfume | 0.60 g |
| Absolute ethyl alcohol | 20.00 g |
| Isopropyl palmitate | 5.00 g |
| Trichlorofluoromethane | 35.00 g |
| Dichlorodifluoromethane | 35.00 g |
| | 100.00 g |

EXAMPLE 7

An antiperspirant composition packaged under pressure as an aerosol is prepared by admixing the following components:

| | |
|---|---|
| Product of Example B | 4.5 g |
| Colloidal silica | 0.4 g |
| Isopropyl palmitate | 3.6 g |
| Perfume VIC 8 (IFF) | 0.5 g |
| Trichlorofluoromethane | 91.00 g |

The above mixture is introduced into a 100 cm$^3$ aerosol container and is then saturated with $CO_2$ under pressure so as to establish therein a pressure of 4.5 kg/cm$^2$.

A similarly effective antiperspirant composition is prepared by replacing the product of Example B, in the above, with an essentially equivalent amount of the product of Example K or Example P.

EXAMPLE 8

An antiperspirant composition packaged under pressure as an aerosol is prepared by admixing the following components:

| | |
|---|---|
| Product of Example E | 3.00 g |
| Isopropyl myristate | 7.00 g |
| Perfume - F.N. 3082 (IFF) | 0.50 g |
| Colloidal silica | 0.30 g |
| Dichlorotetrafluoroethane | 71.00 g |
| Dichlorodifluoromethane | 68.00 g |

A similarly effective antiperspirant composition is prepared by replacing the product of Example E in the above with an essentially equivalent amount of the product of Example A.

EXAMPLE 9

An antiperspirant composition packaged under pressure as an aerosol is prepared by admixing the following components:

| | |
|---|---|
| Product of Example A | 2.60 g |
| Basic aluminum hydrochloride coated with waxy maize starch hydrolyxed to a Stormer viscosity of 85 (no delay effect) | 2.00 g |
| Isopropyl myristate | 4.00 g |
| Colloidal silica | 0.30 g |
| Perfume E1048 (Aromescence) | 0.70 g |
| Trichlorofluoromethane | 42.60 g |
| Dichlorodifluoromethane | 48.00 g |

A similarly effective antiperspirant composition is prepared by replacing the product of Example A with an essentially equivalent amount of the product of Example V.

EXAMPLE 10

An antiperspirant composition packaged under pressure as an aerosol is prepared by admixing the following components:

| | |
|---|---|
| Product of Example M | 8.00 g |
| Isopropyl palmitate | 3.00 g |
| Perfume - E1048 (Aromescence) | 0.50 g |
| Trichlorofluoromethane | 51.25 g |
| Dichlorodifluoromethane | 37.35 g |

A similarly effective antiperspirant composition is prepared by replacing the product of Example M with an essentially equivalent amount of the product of Example S.

EXAMPLE 11

An antiperspirant composition packaged under pressure as an aerosol is prepared by admixing the following components:

| | |
|---|---|
| Product of Example T | 5.25 g |
| Isopropyl myristate | 3.50 g |
| Perfume - Vervia 7C7 (Creat Aromatiques) | 0.40 g |
| Trichlorofluoromethane | 45.00 g |
| Dichlorodifluoromethane | 45.75 g |

A similarly effective antiperspirant composition is prepared by replacing the product of Example T with an essentially equivalent amount of the product of Example E.

EXAMPLE 12

An antiperspirant composition packaged under pressure as an aerosol is prepared by admixing the following components:

| | |
|---|---|
| Product of Example B | 5.00 g |
| Colloidal silica | 0.30 g |
| Isopropyl palmitate | 4.20 g |
| Perfume - Colmen 13 182 g (Firmenich) | 0.50 g |
| Trichlorofluoromethane | 90.00 g |

The above mixture is introduced into a 100 cm$^3$ aerosol container and then saturated with nitrous oxide under pressure so as to establish therein a pressure of 4.5 kg/cm$^2$.

A similarly effective antiperspirant composition is prepared by replacing the product of Example B with an essentially equivalent amount of the product of Example L or Example Q.

EXAMPLE 13

An antiperspirant composition packaged under pressure as an aerosol is prepared by admixing the following components:

| | |
|---|---|
| Product of Example G | 4.30 g |
| Isopropyl palmitate | 3.00 g |
| Perfume - E1048 (Aromescence) | 0.40 g |
| Colloidal silica | 0.30 g |
| Trichlorofluoromethane | 55.00 g |
| Dichlorodifluoromethane | 37.00 g |

A similarly effective antiperspirant composition is prepared by replacing the product of Example G with an essentially equivalent amount of the product of Example U.

EXAMPLE 14

An antiperspirant composition packaged under pressure as an aerosol is prepared by admixing the following components:

| | |
|---|---|
| Product of Example N | 2.00 g |
| Colloidal silica | 0.20 g |
| Perfume - Colmen 13182 g (Firmenich) | 0.30 g |
| Isopropyl palmitate | 3.00 g |
| Trichlorofluoromethane | 49.50 g |
| Dichlorodifluoromethane | 45.00 g |

A similarly effective antiperspirant composition is prepared by replacing the product of Example N with an essentially equivalent amount of the product of Example O.

EXAMPLE 15

An antiperspirant composition packaged under pressure as an aerosol is prepared by admixing the following components:

| | |
|---|---|
| Product of Example F | 3.00 g |
| Isopropyl myristate | 3.00 g |
| Perfume - Vervia C7 (Creat Aromatiques) | 0.40 g |
| Trichlorofluoromethane | 53.60 g |

-continued

| | |
|---|---|
| Dichlorodifluoromethane | 40.00 g |

A similarly effective antiperspirant composition is prepared by replacing the product of Example F with an essentially equivalent amount of the product of Example R or Example W.

EXAMPLE 16

An antiperspirant talc having the following composition is prepared:

| | |
|---|---|
| Talc | 80.00 g |
| Zinc oxide | 4.00 g |
| Zinc stearate | 6.00 g |
| Colloidal silica | 1.00 g |
| Product of Example O | 8.00 g |
| Perfume | 1.00 g |

EXAMPLE 17

An antiperspirant talc is prepared by mixing and grinding to a powder the following components:

| | |
|---|---|
| Talc | 75.00 g |
| Kaolin | 12.00 g |
| Magnesium stearate | 6.00 g |
| Colloidal silica | 1.00 g |
| Perfume | 1.00 g |
| Product of Example A | 5.00 g |

A similarly effective antiperspirant talc is prepared by replacing the product of Example A with an essentially equivalent amount of the product of Example E, Example Q or Example V.

EXAMPLE 18

An antiperspirant talc having the following composition is prepared:

| | |
|---|---|
| Talc | 85.00 g |
| Titanium oxide | 3.00 g |
| Magnesium carbonate | 1.00 g |
| Calcium carbonate (chalk) | 4.00 g |
| Perfume | 1.00 g |
| Product of Example N | 4.00 g |
| Basic aluminum hydrochloride coated with waxy maize starch hydrolyzed to a Stormer viscosity of 85 (no delay effect) | 1.00 g |

In Examples 3-18 the addition of antiperspirant agents having instantaneous effect provides not only instantaneous protection but also good antiperspirant effectiveness over a period of time. These compositions also exhibit excellent stability characteristics during prolonged storage.

What is claimed is:

1. In an antiperspirant agent consisting of coated microcrystals of an antiperspirant derivative of aluminum selected from the group consisting of basic aluminum hydrochloride and basic aluminum hydrobromide the improvement comprising, as the coating for said antiperspirant derivative of aluminum, starch partially crosslinked by etherification, wherein said partially crosslinked starch contains about one crosslink per 100 to 2000 glucose units present in said starch and wherein the weight ratio of said antiperspirant derivative of aluminum to starch (dry basis) is between 1:10 and 1:1, so as to provide a delayed antiperspirant effect.

2. The antiperspirant agent of claim 1 wherein said starch is partially crosslinked with a bifunctional reagent selected from the group consisting of epihalohydrin, dihalohydrin, dihalogenated ether and dihalogenated lower alkane.

3. The antiperspirant agent of claim 1 wherein said starch is crosslinked with epichlorohydrin.

4. The antiperspirant agent of claim 3 wherein one part by weight of epichlorohydrin is employed per 200-3500 parts by weight of said starch.

5. The antiperspirant agent of claim 1, in the form of a powder, the diameter of the particles of the powder ranging between 10-50 microns.

6. A process for preparing the antiperspirant agent of claim 1 comprising introducing into a current of air produced in an atomizer drier an aqueous gel of said partially crosslinked starch containing in solution said antiperspirant derivative of aluminum, said air being at a temperature ranging from 200°-230° C at the inlet of said drier to 110°-120° C at the outlet of said drier, said aqueous gel having a concentration of partially crosslinked starch between 5-30 weight percent thereof and the weight ratio of antiperspirant derivative of aluminum to starch (dry basis) being between 1:10 and 1:1.

7. The process of claim 6 wherein said aqueous gel is obtained by producing a suspension of said starch in cold water, heating said suspension with agitation to a temperature between 80°-90° C so as to impart fluidity thereto and adding thereto said antiperspirant derivative of aluminum either in crystalline form or in the form of an aqueous solution thereof.

8. The process of claim 6 wherein the concentration of said crosslinked starch in said aqueous gel is between 10-15 weight percent thereof.

9. Antiperspirant composition comprising in a cosmetic vehicle suitable for topical application to human skin, the antiperspirant agent of claim 1 in an amount of 2-8 percent by weight of said composition.

10. The antiperspirant composition of claim 9 wherein said cosmetic vehicle comprises an aerosol propellant and said composition is packaged under pressure in an aerosol container.

11. The antiperspirant composition of claim 10 wherein said aerosol propellant is a chlorofluorinated hydrocarbon.

12. The antiperspirant composition of claim 9 wherein said cosmetic vehicle also includes at least one of a deodorizing bactericide, a perfume, a suspension agent and an emollient.

13. The antiperspirant composition of claim 9 wherein said antiperspirant agent is present in an amount of 3-5 percent by weight of said composition.

14. The antiperspirant composition of claim 9 which also includes another antiperspirant agent.

15. The antiperspirant composition of claim 14 wherein said another antiperspirant agent is a micronized non-coated basic aluminum halide.

16. The antiperspirant composition of claim 1 wherein said another antiperspirant agent is a micronized basic aluminum halide in the form of crystals coated with a starch which rapidly dissolves in water or perspiration.

17. The antiperspirant composition of claim 9 wherein said cosmetic vehicle is talc.

* * * * *